ration, New York, N.Y.
United States Patent [19]

Mewshaw et al.

[11] Patent Number: 4,709,025
[45] Date of Patent: Nov. 24, 1987

[54] BETA-LACTAMS SUBSTITUTED AT C-4 WITH SUBSTITUTED AMINOOXYMETHYL

[75] Inventors: Richard E. Mewshaw, King of Prussia; Thomas J. Commons, Wayne, both of Pa.

[73] Assignee: American Home Products Corporation, New York, N.Y.

[21] Appl. No.: 4,529

[22] Filed: Jan. 20, 1987

[51] Int. Cl.$^4$ ................. C07D 417/12; C07D 417/14; A61K 31/425; A61K 31/55
[52] U.S. Cl. .................................... 540/355
[58] Field of Search ........................... 540/355

[56] References Cited

FOREIGN PATENT DOCUMENTS 96296  5/1983  European Pat. Off. .

OTHER PUBLICATIONS

Sendai et al., J. of Antibiotics 38 346 (1985).
Noguchi et al., J. of Antibiotics 38 346 (1985).

Primary Examiner—Mark L. Berch
Attorney, Agent, or Firm—Richard K. Jackson

[57] ABSTRACT

This invention provides novel antibacterial beta-lactams of the formula:

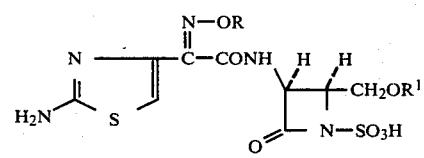

in which
R is alkyl of 1 to 6 carbon atoms, carboxyalkyl of 2 to 6 carbon atoms or alkoxycarbonylalkyl wherein the alkyl and alkoxy moieties contain, independently, 1 to 6 carbon atoms;
$R^1$ is alkylideneamino of 2 to 6 carbon atoms, alkanoylamino of 2 to 6 carbon atoms, carboxyalkylideneamino of 2 to 6 carbon atoms, alkylsulfonylamino of 1 to 6 carbon atoms, alkoxycarbonylalkylsulfonylamino of 3 to 13 carbon atoms, or N,N-cyclodialkanoylamino of 4 to 6 carbon atoms;
or a pharmaceutically acceptable salt thereof.

15 Claims, No Drawings

BETA-LACTAMS SUBSTITUTED AT C-4 WITH SUBSTITUTED AMINOOXYMETHYL

BACKGROUND OF THE INVENTION

European Pat. No. 96,296 discloses a group of 3-iminoacetamido-azetidinone-1-sulfonic acid derivatives with broad spectrum antibacterial properties. Among the substitutional variations embraced at 4-position are the hydroxyiminomethyl and loweralkoxyiminomethyl groups.

Sendai et al., J. of Antibiotics 38 346 (1985), in an attempt to improve the antibacterial activity of sulfazecin, studied various modifications at the 3- and 4-positions, ultimately selecting (3S,4S)-3-[2-(2-aminothiazol-4-yl)-(2)-2-carboxymethoxyiminoacetamido]-4-carbamoyloxymethyl-2-azetidinone-1-sulfonic acid as presenting the best activity profile. Several acyloxymethyl substituents in the 4-position were studied, including the acetoxy-, carbamoyloxy-, benzoyloxy-, methylsulfonyloxy-and 2-thienylacetoxy-methyl groups, with the carbamoyloxy methyl substituent being the most efficient 4-substituent found.

Noguchi et al., J. of Antibiotics 38 1387 (1985) extended the study of 4-position substitutional variations of sulfazecin to explore the 4-acetoxy, methylsulfonyl, various substituted thio groups, azido and triazolyl groups. The 4-carbamoylmethylthio substituent was the most active among the 4-substituted derivatives studied.

DESCRIPTION OF THE INVENTION

In accordance with this invention, there is provided a group of antibacterial agents which are substituted beta-lactams containing an aminooxymethyl substituent in the 4-position, of the formula:

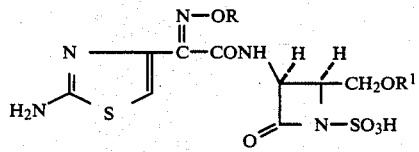

in which

R is alkyl of 1 to 6 carbon atoms, carboxyalkyl of 2 to 6 carbon atoms or alkoxycarbonylalkyl wherein the alkyl and alkoxy moieties contain, independently, 1 to 6 carbon atoms;

$R^1$ is alkylideneamino of 2 to 6 carbon atoms, alkanoylamino of 2 to 6 carbon atoms, carboxyalkylideneamino of 2 to 6 carbon atoms, alkylsulfonylamino of 1 to 6 carbon atoms, alkoxycarbonylalkylsulfonylamino of 3 to 13 carbon atoms, or N,N-cyclodialkanoylamino of 4 to 6 carbon atoms;

or a pharmaceutically acceptable salt thereof.

Of these compounds, the preferred members from the standpoint of production economics and antibacterial potency are those in which R is alkyl of 1 to 3 carbon atoms or carboxyalkyl of 2 to 3 carbon atoms and $R^1$ is alkylsulfonylamino of 1 to 3 carbon atoms, carboxyalkylideneimino of 2 to 3 carbon atoms or succinimido.

The pharmaceutically acceptable salts of the acids of this invention are those of the alkali metals lithium, sodium and potassium, the alkaline earth metals calcium and magnesium, as well as the ammonium salt.

The compounds of this invention are prepared by reacting the known alcohol -cis-2-hydroxymethyl-1-(4-methoxyphenyl)-4-oxo-3-azetidinyl-carbamic acid t-butyl ester with N-hydroxyphthalimide followed by removal of the 1-(4-methoxyphenyl) group by hydrazine to afford the 2-aminooxymethyl substituent. The 2-aminooxymethyl group is then alkylated or acylated, the nitrogen atom in 1-position is sulfonated ($SO_3$.DMF complex), the t-Boc group removed from the nitrogen atom in 3-position with $CF_3CO_2H$ and that nitrogen is acylated with the desired thiazolylacetic acid group. Where the N,N-cyclodialkanoylaminooxymethyl substituent is desired in 2-position, N-hydroxysuccinimide or its homologous analogues are employed initially in lieu of N-hydroxyphthalimide. The pharmaceutically acceptable salts of the so-produced acids are produced conventionally by neutralization of the product acids with the desired base.

The antibacterial activity of the compounds of this invention was established by the microdilution broth method in which the minimum inhibitory concentration (MIC) for a given test compound against a given bacterium is established by inoculating serial dilutions of test compound in broth with a fixed number of the given bacteria per milliliter of broth. The serial dilutions are then incubated for from 18 to 24 hours at 35° C. and the MIC is visually determined and recorded as the lowest test compound dilution in which no bacterial growth is observed.

The results of testing in accordance with the described standard test procedure are as follows:

| Example | E.Cl. | E.c. | K.p. | P.v. | P.a. | S.m. |
|---|---|---|---|---|---|---|
| 7 | 8 | 4 | 4 | 1 | 256 | 8 |
| 8 | 16 | 8 | 4 | 2 | | 16 |
| 9 | 2 | 0.5 | 1 | 0.03 | | 4 |
| 10 | 16 | 2 | 0.5 | 0.125 | 64 | 2 |
| 11 | 32 | 16 | 8 | 1 | | 16 |
| 12 | 8 | 4 | 1 | 0.125 | | 4 |
| 13 | 128 | 64 | 32 | 16 | | 64 |
| 16 | 4 | 4 | 0.5 | 0.5 | 256 | 8 |
| 14 | 128 | 32 | 16 | 1 | 128 | 32 |
| 17 | 16 | 16 | 2 | 0.06 | 8 | 8 |
| 15 | 128 | 128 | 32 | 32 | | 64 |
| 18 | 8* | 8 | 2 | 0.5 | | 4 |
| 19 | | 256 | 128 | 4 | | |
| 20 | 128 | 64 | 32 | 0.5 | 64 | 64 |

Based upon the results obtained in these standard experimental test procedures, the compounds of this invention are characterized as antibacterial agents useful in the treatment of infectious disease states involving pathogenic bacterial as well as in the fields of comparative pharmacology and microbiology for the control and comparative analysis of bacterial colonies. The compounds are to be used in the conventional manner and by the known methods of utilizing beta-lactam antibiotics.

The following examples illustrate the preparation of representative members of the compounds of this invention.

EXAMPLE 1

Preparation of Azetidine Intermediates Phthalimide Route

[Cis-2-[[[(1-methylethylidene)amino]oxy]methyl]-4-oxo-3-azetidinyl]carbamic acid 1,1-dimethylethyl ester To a mixture of cis-2-hydroxymethyl-1-(4-methoxyphenyl)-4-oxo-3-azetidinyl-carbamic acid 1,1-dimethylethyl ester (5.8 g, 18 mmol), N-hydroxyphthalimide (3.0 g, 18 mmole) and triphenylphosphine (5.7 g, 22 mmol) was added diethyl azodicarboxylate (3.7 g, 21 mmol). The reaction was allowed to stir at room temperature for 0.5 hours whereby the solvent was removed in vacuo. The reaction mixture was dissolved in methylene chloride and again the solvent evaporated to remove any residual THF. A solid precipitates and is washed with a solution of methylene chloride-diethyl ether (1:1). The filtrate is concentrated and the solid precipitate is again washed with a solution of methylene chloride-diethyl ether (1:1) and combined with the previously recovered material to afford 5.0 g of [cis-2-[[(1,3-dihydro-1,3-dioxo-2H-isoindol-2-yl)oxy]methyl]-1-(4-methoxyphenyl)-4-oxo-3-azetidinyl]carbamic acid 1,1-dimethylethyl ester (59%). Another 1.9 g (22.3%) of product could be recovered after concentration of the filtrate followed by flash chromatography (ethyl acetate-hexane, 1:9): mp 188°–189° C.; IR (KBr) 3435, 2980, 1795, 1735, 1710, 1500, 1390, 1370, 1160, and 1130 cm$^{-1}$; NMR(CDCl$_3$) δ 1.48 (9H, s), 3.74 (3H, s), 4.40 (1H, br d, J=12 Hz), 4.52 (1H, m), 4.98 (1H, br d, J=12 Hz), 5.44 (1H, m), 6.22 (1H, d, J-9 Hz, exchangeable), 6.82 (2H, d, J=8 Hz), 7.43 (2H, d, J=8 Hz), 7.78 (4H, m).

Analysis for: $C_{24}H_{25}O_7N_3$; Calculated: C, 61.79; H, 5.34; N, 8.97. Found: C, 61.84; H, 5.36; N, 8.88.

[Cis-2-[[(1,3-dihydro-1,3-dioxo-2H-isoindol-2-yl)oxy]-methyl]4-oxo-3-azetidinyl]carbamic acid 1,1-dimethylethyl ester To a solution of the phthalimide produced in the preceding paragraph (5.1 g, 10.9 mmol) in acetonitrile (150 ml) at 0° C. was slowly added a solution of ceric ammonium nitrate (17.9 g, 32.6 mmol) in water (125 ml) to remove the N-4-methoxyphenyl group. The reaction was allowed to stir for another 0.5 hours after addition was complete whereupon the reaction mixture was diluted with 200 ml of water and washed with ethyl acetate (3×200 ml). The organic layer was washed consecutively with 10% Na$_2$SO$_3$ (100 ml), 5% NaHCO$_3$ (100 ml), brine and dried over anhydrous magnesium sulfate. The solvent as evaporated in vacuo and the solid washed with diethyl ether to afford 2.96 g of the [cis-2-[[(1,3-dihydro-1,3-dioxo-2H-isoindol-2-yl)oxy]-methyl]-4-oxo-3-azetidinyl]carbamic acid 1,1-dimethylethyl ester (75%): mp 218°–219° C. (CH$_2$Cl$_2$); IR (KBr) 3325, 2920, 1775, 1730, 1680, 1525, and 1370 cm$^{-1}$; NMR (DMSO-d$_6$) δ 1.36 (9H, s), 4.08 (1H, m), 4.30 (2H, m), 4.97 (1H, dd, J=9,6 Hz), 7.62 (1H, d, J=9 Hz, exchangeable), 7.90 (4H, s), 7.60 (1H, s, exchangeable); FAB HRMS, m/e 384.1208 (MNa$^+$ calculated for $C_{17}H_{19}O_6N_3Na$: 384.1172).

[Cis-2-[(aminooxy)methyl]-4-oxo-3-azetidinyl]carbamic acid 1,1-dimethylethyl ester To the phthalimide produced in the preceding paragraph (2.9 g, 8 mmol) in a solution of methanol-methylene chloride (1:20) at 0° C. was added hydrazine monohydrate (0.78 ml, 16 mmol) to remove phthalic acid and obtain the 2-aminooxymethyl group (oxyamine). The reaction was allowed to stir 1 hour whereupon the reaction was allowed to warm to room temperature. The insoluble impurities were filtered and washed with methylene chloride. The filtrate was concentrated and the solid material was washed with a solution of methanol-methylene chloride (1:20). The filtrate was again concentrated and the solid material was washed with diethyl ether to afford 1.69 g of the [cis-2-[(aminooxy)-methyl]-4-oxo-3-azetidinyl]carbamic acid 1,1-dimethylethyl ester (91%): mp 158°–159° C. (CH$_2$Cl$_2$): IR (KBr) 3350, 3250, 1775, 1690, 1530, 1330, and 1165 cm$^{-1}$; NMR (DMSO-d$_6$) δ 1.40 (9H, s), 3.60 (2H, m), 3.82 (1H, m), 4.86 (1H, dd, J=9, 5 Hz), 6.07 (2H, s, exchangeable), 7.58 (1H, d, J=9 Hz), exchangeable), 8.32 (1H, s, exchangeable).

Analysis for: $C_9H_{17}O_4N_3$: Calculated: C, 46.88; H, 7.34; N, 18.14. Found: C, 46.60; H, 7.61; N, 17.98.

The oxyamine produced in the preceding paragraph (150 mg, 0.65 mmol) was dissolved in acetone (20 ml) and allowed to stir for 10 minutes. The solvent was then evaporated in vacuo and the solid washed with diethyl ether (40 ml) to afford [cis-2-[[[(1-methylethylidene)amino]oxy]methyl]-4-oxo-3-azetidinyl]carbamic acid 1,1-dimethylethyl ester (171 mg, 97%): IR (KBr) 3350, 3220, 2980, 1775, 1690, 1525, 1365, and 1330 cm$^{-1}$; NMR (CDCl$_3$) δ 1.25 (9H, s), 1.86 (3H, s), 1.88 (3H, s), 4.04 (1H, m), 4.17 (1H, dd, J=12, 6 Hz), 4.35 (1H, dd, J=12, 4 Hz), 5.22 (1H, dd, J=9, 6 Hz), 5.36 (1H, d, J=9 Hz, exchangeable), 5.90 (1H, s, exchangeable); FAB HRMS, m/e 272.1596 (MH$^+$ calculated for $C_{12}H_{22}O_4N_3$: 272.1610).

EXAMPLE 2

[Cis-2-[[(acetylamino)oxy]methyl]-4-oxo-3-azetidinyl]-carbamic acid 1,1-dimethylethyl ester To the oxyamine produced in Example 1 (400 mg, 1.73 mmol) dissolved in a solution of CH$_2$Cl$_2$-DMF (1:1) at 0° C. was added pyridine (1.1 eq.) followed by acetyl chloride (1.1 eq.). The reaction was allowed to stir for 15 minutes followed by removal of the solvents under reduced pressure. The residue obtained was purified by flash chromatography (5% CH$_3$OH in CH$_2$Cl$_2$ to 10% CH$_3$OH in CH$_2$Cl$_2$) to afford [cis-2-[[(acetylamino)oxy]methyl]-4-oxo-3-azetidinyl]carbamic acid 1,1-dimethylethyl ester (418 mg, 88.6%): IR (KBr) 3290, 2980, 1760, 1690, 1365, and 1160 cm$^{-1}$; NMR (80 MHz, DMSO-d$_6$) δ 1.40 (9H, s), 1.73 (3H, s), 3.83 (3H, m), 4.90 (1H, dd, J=9, 5 Hz), 7.60 (1H, d, J=9 Hz, exchangeable), 8.55 (1H, s, exchangeable); FAB HRMS, m/e 274.1400 (MH$^+$ calculated for $C_{11}H_{20}O_5N_3$: 274.1403).

EXAMPLE 3

[Cis-2-[[[(methylsulfonyl)amino]oxy]methyl]-4-oxo-3-azetidinyl]carbamic acid 1,1-dimethylethyl ester To a solution of the oxyamine produced in Example 1 (485 mg, 2.1 mmol) in methylene chloride (40 ml) containing pyridine (4 ml) at 0° C. was added methanesulfonyl chloride (1.2 eq.). The reaction was allowed to stir for 1 hour whereupon it was poured into a solution of THF-EtOAc (1:1, 100 ml) and washed with 1N HCl (30 ml). The aqueous layer was extracted with another solution of THF-EtOAc (1:1, 50 ml) and the combined organic layers washed with water, 5% NaHCO$_3$, and brine. The organic layer was dried over anhydrous magnesium sulfate and the solvent concentrated in vacuo to afford a yellow oil. The product was purified using flash chromatography (CH$_3$OH-CH$_2$Cl$_2$, 2:25) to afford [cis-2-[[[(methylsulfonyl)amino]methyl]-4-oxo-3-azetidinyl]carbamic acid 1,1-dimethylethyl ester (414 mg, 64%): mp 157°–158° C. (CH$_2$Cl$_2$); IR (KBr) 3340, 3210, 2970, 1780, 1687, 1525, 1330, and 1160 cm$^{-1}$; NMR (DMSO-d$_6$) δ 1.40 (9H, s), 3.03 (3H, s), 3.84–4.08 (3H, m), 4.94 (1H, dd, J=9, 5 Hz), 7.68 (1H, d, J=9 Hz, exchangeable), 8.44 (1H, s, exchangeable).

Analysis for: $C_{10}H_{19}N_3O_6S$; Calculated: C, 38.95; H, 6.14; N, 13.57. Found: C, 39.09; H, 6.26; N, 13.28.

EXAMPLE 4

[[[Cis-3-[[(1,1-dimethylethoxy)carbonyl]amino]-4-oxo-2-azetidinyl]methoxy]imino]acetic acid A solution of the oxyamine produced in Example 1 (637 mg, 2.75 mmol) and glyoxylic acid monohydrate (295 mg, 3.20 mmol) in THF (25 ml) was allowed to stir for 1 hour. The solvent was removed under reduced pressure and the resulting solid triturated with a solution of methanol-methylene chloride (1:20) to afford [[[cis-3-[[(1,1-dimethylethoxy)carbonyl]amino]-4-oxo-2-azetidinyl]methoxy]imino]acetic acid (630 mg, 79%): IR (KBr) 3325, 2960, 1755, 1705, 1685, 1595, 1515, 1330, 1265, and 1155 cm$^{-1}$; NMR (DMSO-d$_6$) δ 1.40 (9H, s), 3.86 (1H, m), 4.25 (2H, m), 4.88 (1H, dd, J=9, 5 Hz), 7.59 (1H, s), 7.65 (1H, d, J=9 Hz, exchangeable), 8.40 (1H, s, exchangeable); FAB HRMS, m/e 288.1194 (M+ calculated for $C_{11}H_{18}O_6N_3$: 288.1195).

EXAMPLE 5

[[[[Cis-3-[[(1,1-dimethylethoxy)carbonyl]amino]-4-oxo-2-azetidinyl]methoxy]amino]sulfonyl]acetic acid methyl ester To a solution of the oxyamine produced in Example 1 (495 mg, 2.1 mmol) in dry THF containing pyridine (1.1 eq.) was added ClSO$_2$CH$_2$CO$_2$CH$_3$ and the solution was stirred for 1 hour at 0° C. The reaction mixture was diluted with ethyl acetate and washed with 1N HCl, 5% sodium bicarbonate, brine and dried over anhydrous magnesium sulfate. The product was purified by flash chromatography (ethyl acetate-hexane, 1:2) to afford 426 mg (54%) of [[[[cis-3-[[(1,1-dimethylethoxy)carbonyl]amino]-4-oxo-2-azetidinyl]methoxy]amino]sulfonyl]acetic acid methyl ester: mp 128°–129° C. (CH$_2$Cl$_2$); IR (KBr) 3340, 3210, 2975, 1780, 1740, 1685, 1525, and 1160 cm$^{-1}$; NMR (DMSO-d$_6$) δ 1.40 (9H, s), 3.75 (3H, s), 3.90 (1H, m), 4.00 (2H, m), 4.34 (1H, d, J=15 Hz), 4.42 (1H, d, J=15 Hz), 4.94 (1H, d, J=9, 6 Hz), 7.68 (1H, d, J=9 Hz, exchangeable), 8.44 (1H, s, exchangeable).

Analysis for: $C_{12}H_{21}N_3O_8S$; Calculated: C, 39.36; H, 5.71; N, 11.42. Found: C, 39.19; H, 5.86; N, 11.66.

EXAMPLE 6

Preparation of Azetidine Intermediates Succinimide Route

The procedure followed in Example 1 may also be used employing N-hydroxysuccinimide rather than N-hydroxyphthalimide to obtain the following key intermediate: [cis-2-[[(2,5-dioxo-1-pyrrolidinyl)oxy]methyl]-4-oxo-3-azetidinyl]carbamic acid 1,1-dimethylethyl ester. To a mixture of cis-2-hydroxymethyl-1-[4-methoxyphenyl)-4-oxo-3-azetidinyl-carbamic acid 1,1-dimethylethyl ester (1.0 g, 3.1 mmol), N-hydroxysuccinimide (392 mg, 3.4 mmol) and triphenylphosphine (977 mg, 3.7 mmol) in dry THF (25 ml) was added diethyl azodicarboxylate (650 mg, 3.7 mmol). The reaction was allowed to stir for 1 hour whereupon the solvent was removed under reduced pressure. The remaining residue was purified by flash chromatography (benzene-ethyl acetate, 1:1) to afford [cis-2-[[(2,5-dioxo-1-pyrrolidinyl)oxy]methyl]-1-(4-methoxyphenyl)-4-oxo-3-azetidinyl]carbamic acid 1,1-dimethyl ethyl ester (1.07 g, 82%): mp 168°–169° C. (isopropyl ether-methylene chloride); IR (KBr) 3340, 2980, 1755, 1720, 1510, 1380, 1340, and 1245 cm$^{-1}$; NMR (DMSO-d$_6$) δ 1.42 l (9H, s), 2.62 (4H, s), 3.76 (3H, s), 4.38 (2H, m), 4.64 (1H, m), 5.22 (1H, dd, J=9, 6 Hz), 6.98 (2H, d, J=10 Hz), 7.56 (2H, d, J=10 Hz), 7.66 (1H, d, J=9 Hz).

Analysis for: $C_{20}H_{25}N_3O_7$; Calculated: C, 57.40; H, 5.95; N, 10.00. Found: C, 57.20; H, 5.96; N, 9.55.

To a solution of the siccinimide produced in the preceding paragraph in acetonitrile at 0° C. was slowly added a solution of ceric ammonium nitrate in water, to remove the N-4-methoxyphenyl group. The solution was stirred for about 0.5 hours, quenched with water and washed with ethyl acetate. The organic layer was purified following the procedure of Example 1 and the title compound was recovered (87% yield): mp 206.5°–208° C. (dec., ethyl acetate); IR (KBr) 3350, 2975, 1770, 1720, 1685, and 1420 cm$^{-1}$; NMR (DMSO-d$_6$) δ 1.50 (9H, s), 2.62 (4H, s), 3.95 (1H, m), 4.10 (2H, m), 4.95 (1H, dd, J=9, 6 Hz), 7.62 (1H, d, J=9 Hz, exchangeable), 8.55 (1H, s).

Analysis for: $C_{13}H_{19}N_3O_6$; Calculated: C, 49.96; H, 6.06; N, 13.39. Found: C, 50.04; H, 6.05; N, 13.43.

The intermediates produced in Examples 1–5 are sulfonated, N-:deprotected and N-acylated according to the following procedural steps employing the product of Example 1 as representative of the other intermediates of Examples 2 to 5.

EXAMPLE 7

Cis-3-[[(Z)-(2-amino-4-thiazolyl)(methoxyimino)acetyl]amino]-2-[[[(1-methylethylidene)amino]oxy]methyl]-4-oxo-1-azetidine sulfonic acid To a solution of the product of Example 1 (1.5 mmol) in dry DMF (3 ml) was added sulfur trioxide-DMF complex (5 eq.) and the solution was stirred for 2 hours. The reaction mixture was diluted with CH$_2$Cl$_2$ (30 ml) and 1N potassium hydrogen phosphate (15 ml). The pH was adjusted to approximately 6, followed by the addition of tetrabutylammonium hydrogen sulfate (1.0 eq.). The layers were separated and the aqueous layer extracted again with CH$_2$Cl$_2$ (2×20 ml). The combined organic layers were dried over anhydrous magnesium sulfate. The solvent was evaporated in vacuo to afford [cis-2[[[(1-methylethylidene)amino]oxy]methyl]-3-tertiarybutyloxycarbonylamino-4-oxo-1-azetidinyl]sulfonic acid tetrabutylammonium salt (84% yield).

The tetrabutylammonium salt prepared in the preceding paragraph was added to a cold solution (0° C.) of trifluoroacetic acid (7 ml) containing anisole (1.5 ml). The reaction was allowed to stir for 3 hours whereupon cold toluene (10 ml) was added and the solvents removed under reduced pressure. Additional toluene was added and distilled to remove any residual TFA. The solid residue was washed with methylene chloride (2×10 ml) to afford [cis-3-amino-2-[[[(1-methylethylidene)amino]oxy]methyl]-4-oxo-1-azetidinyl]sulfonic acid. The reaction product may alternatively be worked up by addition of diethyl ether (30 ml) and filtration of the precipitate which is washed with methylene chloride (10 ml).

A solution of N-hydroxybenzotriazole hydrate (1 mmol) and 2-(2-amino-4-thiazolyl)-2-(methoxyimino) acetic acid (1 mmol) in DMF (7 ml) was treated with diisopropylcarbodiimide (1.1 mmol) under nitrogen at ambient temperature. The reaction mixture is stirred for 45 minutes, at which time the 3-amino-2-substituted-4- oxo-1-azetidinesulfonic acid derivative prepared in the preceding paragraph (1 mmol) was added in a solution of DMF (2 ml) containing triethylamine (2 mmol). The reaction was stirred for 17 hours after which time the DMF was removed under reduced pressure. The residue was taken up in acetone (8 ml) and any insoluable material was filtered off. To this acetone solution was added potassium nonafluorobutanesulfonate (1 mmol) in acetone (previously filtered before addition). The precipitate was filtered and washed with acetone (10 ml) followed by diethyl ether (5 ml) to afford the title compound as the potassium salt. Sixty percent (60%) yield; IR (KBr) 3400, 1765, 1670, 1530, 1050 cm$^{-1}$; NMR (DMSO-d$_6$) δ 1.74 (3H, s), 1.82 (3H, s), 3.84 (3H, s), 4.10 (2H, m), 4.42 (1H, app. d, J=9 Hz), 5.00 (1H, dd, J=9, 5 Hz), 6.74 (1H, s), 7.25 (2H, br s, exchangeable), 9.34 (1H, d, J=9 Hz, exchangeable); FAB HRMS, m/e 433.0595 (M+ calculated for C$_{13}$H$_{17}$O$_7$N$_6$S$_2$: 433.0600).

EXAMPLE 8

2-[[(Acetylamino)oxy]methyl]-3-[[(2-amino-4-thiazolyl)(methoxyimino)acetyl]amino]-4-oxo-1-azetidinesulfonic acid Following the procedure of Example 7, the title compound was produced as the potassium salt from the product of Example 2. Sixty-two percent (62%) yield; IR (KBr) 3400, 1765, 1660, 1525, 1045 cm$^{-1}$; NMR (DMSO-d$_6$) δ 1.70 (3H, s), 3.82 (3H, s), 3.88 (1H, m), 4.04–4.32 (2H, m), 5.32 (1H, dd, J=9, 6 Hz), 6.80 (1H, s), 7.20 (2H, br s, exchangeable), 9.44 (1H, d, J=9 Hz, exchangeable).

EXAMPLE 9

3-[[(2-amino-4-thiazolyl)(methoxyimino)acetyl]amino]2-[[[(methylsulfonyl)amino]oxy]methyl]-4-oxo-1-azetidinesulfonic acid Following the procedure of Example 7, the title compound was produced as the potassium salt, from the product of Example 3. Forty-seven percent (47%) yield; IR (KBr) 3440, 3320, 1765, 1665, 1610, 1530, 1160, 1045 cm$^{-1}$; NMR (DMSO-d$_6$) δ 3.00 (3H, s), 3.87 (3H, s), 4.09–4.14 (3H, m), 5.27 (1H, dd, J=9, 5 Hz), 6.81 (1H, s), 7.25 (2H, br s, exchangeable), 9.28 (1H, d, J=9 Hz, exchangeable), 9.97 (1H, br s, exchangeable); FAB HRMS, m/e 471.0063 (M+-K calculated for C$_{11}$H$_{15}$O$_9$N$_6$S$_3$: 471.0062).

EXAMPLE 10

[[[3-[[(2-amino-4-thiazolyl)(methoxyimino)acetyl]amino]-4-oxo-1-sulfo-2-azetidinyl]methoxy]imino]acetic acid Following the procedure of Example 7, the title compound was prepared as the dipotassium salt, from the product of Example 4. Twenty-eight percent (28%) yield; IR (KBr) 3350, 1765, 1660, 1620, 1210, 1050 cm$^{-1}$; NMR (DMSO-d$_6$) δ 3.84 (3H, s), 4.10–4.25 (2H, m), 4.42 (1H, m), 5.22 (1H, dd, J=9, 5 Hz), 6.78 (1H, s), 7.27 (2H, br s, exchangeable), 7.32 (1H, s), 9.34 (1H, d, J=9 Hz, exchangeable).

Analysis for: C$_{12}$H$_{12}$N$_6$O$_9$S$_2$K$_2$H$_2$O; Calculated: C, 26.56; H, 2.39; N, 15.42. Found: C, 26.67; H, 2.57; N, 15.36.

EXAMPLE 11

[[[3-[[(2-amino-4-thiazolyl)(methoxyimino)acetyl]amino]-4-oxo-1-sulfo-2-azetidinyl]methoxy]amino]sulfonyl]acetic acid methyl ester Following the procedure of Example 7, the title compound was prepared as the potassium salt, from the product of Example 5. Seventy-five percent (75%) yield; IR (KBr) 3320, 1755, 1665, 1525, 1045 cm$^{-1}$; NMR (DMSO-d$_6$) δ 3.72 (3H, s), 3.84 (3H, s), 4.05–4.44 (5H, m), 5.25 (1H, dd, J=9, 5 Hz), 6.77 (1H, s), 7.24 (2H, br s, exchangeable), 9.26 (1H, d, J=9 Hz, exchangeable); FAB HRMS, m/e 529.0052 (M+-K calculated for C$_{13}$H$_{17}$N$_6$O$_{11}$S$_3$: 529.0117.

EXAMPLE 12

3-[[(2-amino-4-thiazolyl)methoxyimino)acetyl]amino]-2-[[2,5-dioxo-1-pyrrolidinyl)oxy]methyl]-4-oxo-1-azetidinesulfonic acid Sulfonation, deprotection and acylation of the product of Example 6, following the procedure of Example 7, affords the title compound as a potassium salt. Sixty percent (60%) yield; IR (KBr) 3420, 1765, 1715, 1665, 1525, 1045 cm$^{-1}$; NMR (DMSO-d$_6$) δ 2.60 (4H, s), 3.87 (3H, s), 4.27–4.44 (3H, m), 5.26 (1H, dd, J=9, 5 Hz), 6.84 (1H, s), 7.23 (2H, br s, exchangeable), 9.12 (1H, d, J=9 Hz, exchangeable).

Analysis for: C$_{14}$H$_{15}$N$_6$O$_9$SK½H$_2$O; Calculated: C, 32.22; H, 3.24; N, 16.03. Found: C, 32.52; H, 3.48; N, 16.25.

EXAMPLE 13

[[[1-(2-amino-4-thiazolyl)-2-[[2-[[[(methylsulfonyl)amino]oxy]methyl]4-oxo-1-sulfo-3-azetidinyl]amino]-2-oxoethylidene]amino]oxy]acetic acid 1,1-dimethylethyl ester Sulfonation, removal of the t-Boc protecting group, and acylation of the product of Example 3 with 2-(1-amino-4-thiazolyl)-2-(tertiary butyloxycarbonylmethyloxyimino) acetic acid following the procedure of Example 7 affords the title compound as the potassium salt. Fifty-three percent (53%) yield; IR (KBr) 3440, 3325, 2980, 1760, 1670, 1615, 1530, 1160, 1050 cm$^{-1}$; NMR (DMSO-d$_6$) δ 1.44 (9H, s), 2.94 (3H, s), 4.08–4.45 (3H, m), 4.56 (2H, s), 5.26 (1H, dd, J=9, 5 Hz), 6.82 (1H, s), 7.24 (2H, br s, exchangeable), 9.28 (1H, d, J=9 Hz, exchangeable).

Analysis for: C$_{16}$H$_{23}$N$_6$O$_{11}$S$_3$KCH$_3$CO$_2$H; Calculated: C, 32.35; H, 4.02; N, 12.52. Found: C; 32.67; H, 3.95; N, 12.75.

EXAMPLE 14

[[[1-(2-amino-4-thiazolyl)-2-[[2-[[[(carboxymethylene)amino]oxy]methyl]-4-oxo-1-sulfo-3-azetidinyl]amino]-2-oxyethylidene]amino]oxy]acetic acid 1,1-dimethylethyl ester Sulfonation, removal of the t-Boc protecting group and acylation of the product of Example 4 with 2-(2-amino-4-thiazolyl)-2-(tertiarybutyloxycarbonylmethyloxyimino)acetic acid following the procedure of Example 7, affords the title compound as the dipotassium salt. Fifty-nine percent (59%) yield; IR (KBr) 3420, 2985, 1760, 1660, 1615, 1045 cm$^{-1}$; NMR (DMSO-d$_6$) δ 1.44 (9H, s), 4.10–4.64 (5H, m), 5.26 (1H, dd, J=9, 5 Hz), 6.80 (1H, s), 7.20 (2H, br s, exchangeable), 7.40 (1H, s), 9.34 (1H, d, J=9 Hz).

EXAMPLE 15

[[[1-(2-amino-4-thiazolyl)-2-[[2-[[(2,5-dioxo-1-pyrrolidinyl)oxy]methyl]-4-oxo-1-sulfo-3-azetidinyl]amino]-2-oxoethylidene]amino]oxy]acetic acid 1,1-dimethylethyl ester Sulfonation, deprotection and acylation of the product of Example 6 with 2-(2-amino-4-thiazolyl)-2-(tertiarybutyloxycarbonylmethyloxyimino)acetic acid following the procedure of Example 7, affords the title compound as the potassium salt. Forty-five percent (45%) yield; IR (KBr) 3420, 1760, 1715, 1665, 1520, 1045 cm$^{-1}$; NMR (DMSO-d$_6$) δ 1.45 (9H, s), 2.60 (4H, s), 4.08–4.60 (5H, m), 5.26 (1H, dd, J=9, 5 Hz), 6.85 (1H, s), 7.26 (2H, br s, exchangeable), 9.12 (1H, d, J=9 Hz, exchangeable).

EXAMPLE 16

[[[1-(2-amino-4-thiazolyl)-2-[[2-[[[(methylsulfonyl)amino]oxy]methyl]4-oxo-1-sulfo-3-azetidinyl]amino]-2-oxoethylidene]amino]acetic acid Sulfonation, removal of the t-Boc protecting group following the alternative workup procedure with diethyl ether, and acylation of the product of Example 3 with 2-(2-amino-4-thiazolyl)-2-(carboxymethyloxyimino)acetic acid following the procedure of Example 7 affords the title compound as the potassium salt, trifluoroacetate. Twenty percent (20%) yield; IR (KBr) 3360, 1760, 1660, 1625, 1040 cm$^{-1}$; NMR (DMSO-d$_6$) δ 3.00 (3H, s), 3.78–4.38 (3H, m), 4.64 (2H, s), 5.28 (1H, dd, J=9, 5 Hz), 6.90 (1H, s), 9.38 (1H, d, J=9 Hz, exchangeable), 9.98 (1H, s, exchangeable); FAB HRMS, m/e 514.9957 (M$^+$-K calculated for C$_{12}$H$_{15}$O$_{11}$N$_6$S$_3$: 514.9961).

Analysis for: C$_{12}$H$_{15}$N$_6$O$_{11}$SKCF$_3$CO$_2$H: Calculated: C, 25.24; H, 2.39; N, 12.56. Found: C, 25.60; H, 2.99; N, 12.27.

EXAMPLE 17

[[[1-(2-amino-4-thiazolyl)-2-[[[(carboxymethylene)amino]oxy]methyl]4-oxo-1-sulfo-3-azetidinyl]amino]-2-oxoethylidene]amino]oxy]acetic acid Sulfonation, removal of the t-Boc protecting group following the alternative workup procedure with diethyl ether and acylation of the product of Example 4 with 2-(2-amino-4-thiazolyl)-2-(carboxymethyloxyimino)acetic acid, following the procedure of Example 7 affords the title compound as the potassium salt, trifluoroacetate. Seventy-four percent (74%) yield; IR (KBr) 3350, 1755, 1655, 1625, 1040 cm$^{-1}$; NMR (DMSO-d$_6$) δ 4.12–4.80 (5H, m), 5.32 (1H, dd, J=9, 5 Hz), 6.81 (1H, s), 7.58 (1H, s, exchangeable), 9.42 (1H, d, J=9 Hz).

EXAMPLE 18

[[[1-(2-amino-4-thiazolyl)-2-[[2-[[(2,5-dioxo-1-pyrrolidinyl)oxy]methyl]4-oxo-1-sulfo-3-azetidinyl]amino]-2-oxoethylidene]amino]oxy]acetic acid Sulfonation, removal of the t-Boc protecting group following the alternative workup procedure with diethyl ether and acylation of the product of Example 6 with 2-(2-amino-4-thiazolyl)-2-(carboxymethyloxyimino)acetic acid, following the procedure of Example 7, affords the title compound as the potassium salt, trifluoroacetate. Sixty-nine percent (69%) yield; IR (KBr) 3300, 1765, 1715, 1670, 1045 cm$^{-1}$; NMR (DMSO-d$_6$) δ 2.60 (4H, s), 4.34 (1H, m), 4.46 (1H, m), 5.30 (1H, dd, J=9, 5 Hz), 6.98 (1H, s), 9.12 (1H, d, J=9 Hz, exchangeable).

EXAMPLE 19

2-[[[1-(2-amino-4-thiazolyl)-2-[[2-[[[(carboxymethylene)amino]oxy]methyl]4-oxo-1-sulfo-3-azetidinyl]amino]-2-oxoethylidene]amino]oxy]2-methylpropanoic acid, 1,1-dimethylethyl ester Sulfonation, deprotection and acylation of the product of Example 4 with 2-(2-amino-4-triazolyl)-2-(1-tertiarybutyloxycarbonyl-1-methylethoxyimino)acetic acid, following the procedure of Example 7, affords the title compound as the potassium salt. Sixty-five percent (65%) yield; IR (KBr) 3320, 1765, 1715, 1675, 1615, 1325, 1245, 1050 cm$^{-1}$; NMR (DMSO-d$_6$) δ 1.40 (15H, s), 4.12–5.60 (3H, m), 5.26 (1H, dd, J=9, 5 Hz), 6.72 (1H, s), 7.30 (2H, br s, exchangeable), 7.45 (1H, s), 9.12 (1H, d, J=9 Hz, exchangeable).

EXAMPLE 20

2-[[[1-(2-amino-4-thiazolyl)-2-[[2-[[[(carboxymethylene)amino]oxy]methyl]-4-oxo-1-sulfo-3-azetidinyl]amino]-2-oxoethylidene]amino]oxy]-2-methylpropanoic acid Sulfonation, removal of the t-Boc protecting group following the alternative workup procedure with diethyl ether and acylation of the product of Example 4 with 2-(2-amino-4-thiazolyl)-2-(1-carboxy-1-methylethoxyimino)acetic acid as the potassium salt, trifluoroacetate. Fifty percent (50%) yield; IR (KBr) 3200, 1775, 1725, 1675, 1050 cm$^{-1}$; NMR (DMSO-d$_6$) δ 1.42 (6H, s), 4.50–4.64 (3H, m), 5.30 (1H, dd, J=9, 5 Hz), 6.76 (1H, s), 7.58 (1H, s), 9.22 (1H, d, J=9 Hz, exchangeable); FAB HRMS, m/e 521.0380 (M$^+$-K-CF$_3$CO$_2$H calculated for C$_{15}$H$_{17}$O$_{11}$N$_6$S$_2$: 521.0397).

What is claimed is:

1. A compound of the formula:

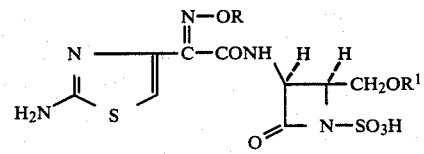

in which

R is alkyl of 1 to 6 carbon atoms, carboxyalkyl of 2 to 6 carbon atoms or alkoxycarbonylalkyl wherein the alkyl and alkoxy moieties contain, independently, 1 to 6 carbon atoms;

R$^1$ is alkylideneamino of 2 to 6 carbon atoms, alkanoylamino of 2 to 6 carbon atoms, carboxyalkylideneamino of 2 to 6 carbon atoms, alkylsulfonylamino of 1 to 6 carbon atoms, alkoxycarbonylalkylsulfonylamino of 3 to 13 carbon atoms, or N,N-cyclodialkanoylamino of 4 to 6 carbon atoms;

or a pharmaceutically acceptable salt thereof.

2. A compound of claim 1 of the formula Cis-3-[[(Z)-(2-amino-4-thiazolyl)(methoxyimino)acetyl]amino]-2-[[[(1-methylethylidene)amino]oxy]methyl]-4-oxo-1-azetidine sulfonic acid, or a pharmaceutically acceptable salt thereof.

3. A compound of claim 1 of the formula 2-[[(Acetylamino)oxy]methyl]-3-[[(2-amino-4-thiazolyl)-

(methoxyimino)acetyl]amino]-4-oxo-1-azetidinesulfonic acid, or a pharmaceutically acceptable salt thereof.

4. A compound of claim 1 of the formula 3-[[(2-amino-4-thiazolyl)(methoxyimino)acetyl]amino]-2-[[[(methylsulfonyl)amino]oxy]methyl]-4-oxo-1-azetidinesulfonic acid, or a pharmaceutically acceptable salt thereof.

5. A compound of claim 1 of the formula [[[3-[[(2-amino-4-thiazolyl)(methoxyimino)acetyl]amino]-4-oxo-1-sulfo-2-azetidinyl]methoxy]imino]acetic acid, or a pharmaceutically acceptable salt thereof.

6. A compound of claim 1 of the formula [[[3-[[(2-amino-4-thiazolyl)(methoxyimino)acetyl]amino]-4-oxo-1-sulfo-2-azetidinyl]methoxy]amino]sulfonyl]acetic acid methyl ester, or a pharmaceutically acceptable salt thereof.

7. A compound of claim 1 of the formula 3-[[(2-amino-4-thiazolyl)methoxyimino)acetyl]amino]-2-[[2,5-dioxo-1-pyrrolidinyl)oxy]methyl]-4-oxo-1-azetidinesulfonic acid, or a pharmaceutically acceptable salt thereof.

8. A compound of claim 1 of the formula [[[1-(2-amino-4-thiazolyl)-2-[[2-[[[(methylsulfonyl)amino]oxy]methyl]4-oxo-1-sulfo-3-azetidinyl]amino]-2-oxoethylidene]amino]oxy]acetic acid 1,1-dimethylethyl ester, or a pharmaceutically acceptable salt thereof.

9. A compound of claim 1 of the formula [[[1-(2-amino-4-thiazolyl)-2-[[2-[[[(carboxymethylene)amino]oxy]methyl]-4-oxo-1-sulfo-3-azetidinyl]amino]-2-oxyethylidene]amino]oxy]acetic acid 1,1-dimethylethyl ester, or a pharmaceutically acceptable salt thereof.

10. A compound of claim 1 of the formula [[[1-(2-amino-4-thiazolyl)-2-[[2-[[(2,5-dioxo-1-pyrrolidinyl)oxy]methyl]-4-oxo-1-sulfo-3-azetidinyl]amino]-2-oxoethylidene]amino]oxy]acetic acid 1,1-dimethylethyl ester, or a pharmaceutically acceptable salt thereof.

11. A compound of claim 1 of the formula [[[1-(2-amino-4-thiazolyl)-2-[[2-[[[(methylsulfonyl)amino]oxy]methyl]-4-oxo-1-sulfo-3-azetidinyl]amino]-2-oxoethylidene]amino]acetic acid, or a pharmaceutically acceptable salt thereof.

12. A compound of claim 1 of the formula [[[1-(2-amino-4-thiazolyl)-2-[[[(carboxymethylene)amino]oxy]methyl]-4-oxo-1-sulfo-3-azetidinyl]amino]-2-oxoethylidene]amino]oxy]acetic acid, or a pharmaceutically acceptable salt thereof.

13. A compound of claim 1 of the formula [[[1-(2-amino-4-thiazolyl)-2-[[2-[[(2,5-dioxo-1-pyrrolidinyl)oxy]methyl]-4-oxo-1-sulfo-3-azetidinyl]amino]-2-oxoethylidene]amino]oxy]acetic acid, or a pharmaceutically acceptable salt thereof.

14. A compound of claim 1 of the formula 2-[[[1-(2-amino-4-thiazolyl)-2-[[2-[[[(carboxymethylene)amino]oxy]methyl]-4-oxo-1-sulfo-3-azetidinyl]amino]-2-oxoethylidene]amino]oxy]-2-methylpropanoic acid, 1,1-dimethylethyl ester, or a pharmaceutically acceptable salt thereof.

15. A compound of claim 1 of the formula 2-[[[1-(2amino-4-thiazolyl)-2-[[2-[[[(carboxymethylene)amino]oxy]methyl]-4-oxo-1-sulfo-3-azetidinyl]amino]-2-oxoethylidene]amino]oxy]-2-methylpropanoic acid, or a pharmaceutically acceptable salt thereof.

* * * * *